United States Patent [19]
Liu

[11] Patent Number: 5,269,807
[45] Date of Patent: Dec. 14, 1993

[54] SUTURE FABRICATED FROM SYNDIOTACTIC POLYPROPYLENE

[75] Inventor: Cheng-Kung Liu, Norwalk, Conn.

[73] Assignee: United States Surgical Corporation, Norwalk, Conn.

[21] Appl. No.: 936,571

[22] Filed: Aug. 27, 1992

[51] Int. Cl.$^5$ .............................................. A61L 17/00
[52] U.S. Cl. .................................... 606/228; 606/151; 606/231; 526/351; 525/240; 525/196; 525/221
[58] Field of Search ................... 623/11, 13; 606/228, 606/230, 231, 151; 526/351; 525/240, 196, 221

[56] References Cited

U.S. PATENT DOCUMENTS

| | | |
|---|---|---|
| 3,258,455 | 6/1966 | Natta et al. |
| 3,268,627 | 8/1966 | Emrick |
| 3,305,538 | 2/1967 | Natta et al. |
| 3,364,190 | 1/1968 | Emrick |
| 3,511,824 | 5/1970 | Listner |
| 3,630,205 | 12/1971 | Listner |
| 4,543,286 | 9/1985 | Harpell et al. ............ 428/413 |
| 4,557,264 | 12/1985 | Hinsch |
| 4,620,542 | 11/1986 | Menzes et al. ............ 523/114 |
| 4,621,638 | 11/1986 | Silvestrini |
| 4,892,851 | 1/1990 | Ewen et al. |
| 4,911,165 | 3/1990 | Lennard et al. |
| 5,132,381 | 7/1992 | Winter et al. |
| 5,200,131 | 4/1993 | Asanumo et al. |

Primary Examiner—Randall L. Green
Assistant Examiner—Paul Prebilic

[57] ABSTRACT

A suture is manufactured from a syndiotactic polypropylene, advantageously by a melt extrusion (spinning) procedure. The suture exhibits greater flexibility than a comparable suture manufactured from isotactic polypropylene.

12 Claims, 2 Drawing Sheets

SUTURE FABRICATED FROM SYNDIOTACTIC POLYPROPYLENE

BACKGROUND OF THE INVENTION

This invention relates to a suture fabricated from syndiotactic polypropylene and to a process for its manufacture.

Sutures fabricated from polypropylene homopolymers and copolymers and from polymer blends containing polypropylene are disclosed in, among others, U.S. Pat. Nos. 3,630,205, 4,621,638 and 4,911,165 (sutures obtained by the melt extrusion of isotactic polypropylene), U.S. Pat. Nos. 4,520,822 and 4,620,542 (sutures made from ethylenepropylene copolymers) and U.S. Pat. No. 4,557,264 (sutures made from blends of polypropylene and linear low density polyethylene).

Syndiotactic polypropylenes, blends containing these resins and fibers produced from the resins are known, e.g., from U.S. Pat. Nos. 3,258,455, 3,268,627, 3,305,538, 3,364,190, 4,892,851 and 5,132,381. U.S. Pat. No. 3,511,824 discloses a monofilament manufactured from an isotactic-randitactic polypropylene defined therein as a macromolecular combination of short length isotactic, syndiotactic and heterotactic polypropylene which is completely soluble in diethyl ether.

SUMMARY OF THE INVENTION

In accordance with the present invention, a suture is fabricated from a syndiotactic polypropylene, advantageously, by a melt extrusion (spinning) process in which the syndiotactic polypropylene is extruded to provide a monofilament, the solidified monofilament is subjected to stretching and the stretched monofilament is subjected to annealing to provide the suture.

The suture of this invention exhibits improved handling characteristics, e.g., greater flexibility, compared with a suture of the same size fabricated entirely from isotactic polypropylene.

DESCRIPTION OF THE PREFERRED EMBODIMENTS

The expression "syndiotactic polypropylene" is used herein to designate a polypropylene in which the methyl groups attached to the tertiary carbon atoms of successive monomeric units in the chain lie on alternate sides of the plane of the polymer. Use of the expression "syndiotactic polypropylene" herein also serves to exclude polypropylenes containing a significant number of non-syndiotactic sequences, e.g., the isotactic-randiotactic polypropylenes of aforementioned U.S. Pat. No. 3,511,824.

Syndiotactic polypropylene resins which can be used to provide the suture of this invention include those described in aforesaid U.S. Pat. Nos. 3,258,455, 3,305,538, 3,364,190, 4,892,851 and 5,132,381, the contents of which are incorporated by reference herein. These resins are characterized, inter alia by a weight average molecular weight of from about 15,000 to about 400,000 and preferably from about 20,000 to about 300,000, a number average molecular weight of from about 4,000 to about 200,000 and preferably from about 5,000 to about 150,000 and a melt flow index in g/10 min of from about 2 to about 20 and preferably from about 3 to about 5. Blends of syndiotactic resins with one or more other thermoplastic resins can also be used, e.g., blends containing from about 5 to about 95 weight percent, and preferably from about 20 to about 80 weight percent, syndiotactic polypropylene, the balance of the blend containing, e.g., isotactic polypropylene, atactic polypropylene, etc. For further details regarding blends of syndiotactic and isotactic polypropylenes, reference may be made to U.S. Pat. No. 3,364,190 the contents of which are incorporated by reference herein.

In general, the conditions of the individual steps of extruding, stretching (orienting) and annealing in the syndiotactic polypropylene monofilament suture manufacturing process of this invention can be substantially the same as those disclosed in U.S. Pat. No. 3,630,205, the contents of which are incorporated by reference herein. Similarly, the process herein can employ much the same type apparatus as that described in U.S. Pat. No. 3,630,205.

Figure 1:
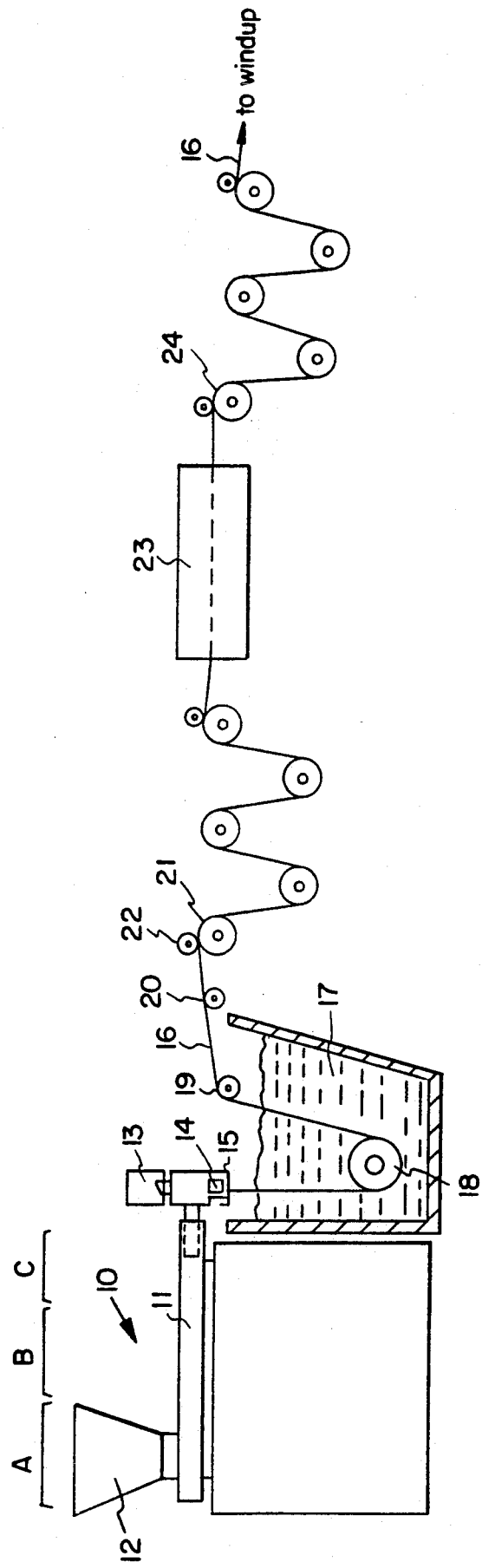
FIG. 1 is a schematic illustration of apparatus which is suitable for carrying out the extruding and stretching steps of the syndiotactic polypropylene monofilament suture manufacturing process of this invention; and, FIG. 2 illustrates a combined suture-surgical needle device in which the suture component is manufactured from a syndiotactic polypropylene in accordance with this invention.

FIG. 1 schematically illustrates the extrusion and stretching operations of the syndiotactic polypropylene monofilament manufacturing operation herein. Extruder unit 10 is of a known or conventional type and is equipped with controls for regulating the temperature of barrel 11 in various zones thereof, e.g., progressively higher temperatures in three consecutive zones A, B and C along the length of the barrel. Pellets or powder of syndiotactic polypropylene resin are introduced to the extruder through drier-hopper 12.

Motor-driven metering pump 13 delivers extruded resin at a constant rate to spin pack 14 and thereafter through spinneret 15 possessing one or more orifices of desired diameter to provide a molten monofilament 16 which then enters quench bath 17, e.g., containing water, where the monofilament solidifies. The distance monofilament 16 travels after emerging from spinneret 15 to the point where it enters quench bath 17, i.e., the air gap, can vary and can advantageously be from about 0.5 to about 100 cm and preferably from about 1 to about 20 cm. If desired, a chimney (not shown), or shield, can be provided to isolate monofilament 16 from contact by air currents which might otherwise affect the cooling o the monofilament in some unpredictable manner. In general, barrel zone A of the extruder can be maintained at a temperature of from about 130° to 200° C., zone B at from about 150° to 220° C. and zone C at from about 170° to about 230° C. Additional temperature parameters include: metering pump block 13 at from about 160° to about 230° C., spin pack 14 at from about 170° to about 230° C., spinneret 15 at from about 170° to about 240° C. and quench bath 17 at from about 20° to about 80° C.

Entering quench bath 17, monofilament 16 is passed by driven roller 18 over idler rollers 19 and 20 and thereafter is wrapped around a first godet 21 provided with nip roll 22 to prevent slippage which might otherwise result from the subsequent stretching operation. Monofilament 16 passing from godet 21 is stretched in order to effect its orientation and thereby increase its tensile strength. Thus, in one type of stretching operation, generally suitable for smaller sutures, e.g., sizes 4/0 to 8/0, monofilament 16 is drawn through heating unit 23, which can be an oven chamber or a hot water trough, by means of second godet 24 which rotates at a higher speed than first godet 21 thereby stretching the monofilament from three to eight times its original length. Where heating unit 23 is an oven chamber, its temperature is advantageously maintained at from about 40° to about 140° C. and preferably from about 60° to about 100° C. In the case of larger sutures, e.g., sizes 2 to 3/0, it is preferred that heating unit 23 be a hot water trough or bath which is maintained at a temperature of from about 40° to about 98° C. and preferably from about 60° to about 98° C.

For smaller suture sizes, e.g., sizes 6/0 to 8/0, it is preferred to pass the monofilament through a second heating unit, e.g., maintained at a temperature of from about 50° to about 130° C. and preferably from about 60° to about 100° C., by means of a third godet to heat-treat the monofilament prior to the equilibration and annealing operations. The second heat treatment results in on-line relaxation, or shrinkage, of the monofilament, e.g., for a recovery of from about 85 to about 97 percent, and preferably from about 90 to about 95 percent, of the stretched length of the monofilament. In order to accommodate this on-line shrinkage in the monofilament, the third godet is driven at a speed which is less than that of the second godet.

In carrying out the annealing operation, the desired length of suture may be wound around a creel and the creel placed in a heating cabinet maintained at the desired temperature, e.g., ranging from 60° to 120° C. as described in U.S. Pat. No. 3,630,205. After a suitable period of residency in the heating cabinet, e.g, about 5 to 30 minutes or so, the suture will have undergone shrinkage, e.g., to about 85% to 90% of the stretched length for sutures of sizes 2 to 3/0, to about 90% to 95% of the stretched length for sutures of sizes 4/0 and 5/0 and essentially no shrinkage in the case of sutures of sizes 6/0 to 8/0. As shown in U.S Pat. No. 3,630,205, the creel may be rotated within the heating cabinet in order to insure uniform heating of the monofilament or the cabinet may be of the circulating hot air type in which case uniform heating of the monofilament will be achieved without the need to rotate the creel. Thereafter, the creel with its annealed suture is removed from the heating cabinet and when returned to room temperature, the suture is removed from the creel, conveniently by cutting the wound monofilament at opposite ends of the creel. The annealed sutures, optionally attached to surgical needles, are then ready to be packaged and sterilized.

Figure 2:
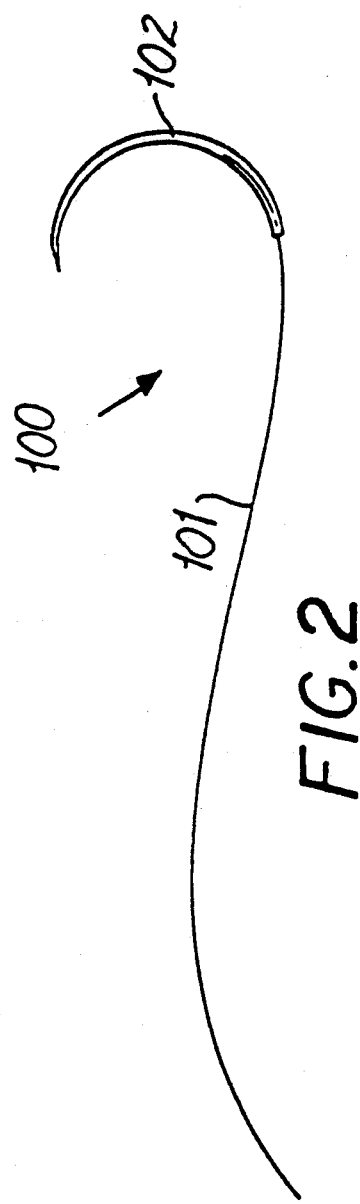

FIG. 2 illustrates a combined suture-surgical needle device 100 in which monofilament suture 101 made from syndiotactic polypropylene is attached to surgical needle 102. Suturing with combined suture-surgical device 100 is accomplished in accordance with accepted surgical practice, i.e., with repeated passes of needle 102 through approximated tissue at the wound site to ligate the wound followed by tying a knot in the suture and removing the needle.

The following examples are illustrative of the syndiotactic polypropylene monofilament suture of this invention and the process for its manufacture.

EXAMPLES 1-10

Table I below sets forth typical conditions for extruding, stretching, optionally heat treating (in the case of suture sizes 6/0 to 8/0) and annealing various sizes of syndiotactic polypropylene monofilament suture in accordance with this invention. In descending order, the size of the sutures range from 2 to 8/0.

TABLE I

| CONDITIONS OF MANUFACTURING VARIOUS SIZES OF POLYPROPYLENE MONOFILAMENT SUTURE | | | | | | | | | | |
|---|---|---|---|---|---|---|---|---|---|---|
| | Example | | | | | | | | | |
| | 1 | 2 | 3 | 4 | 5 | 6 | 7 | 8 | 9 | 10 |
| | Suture Size | | | | | | | | | |
| Process Conditions | 2 | 1 | 0 | 2/0 | 3/0 | 4/0 | 5/0 | 6/0 | 7/0 | 8/0 |
| | Extrusion Operation | | | | | | | | | |
| extruder screw, rpm | 17.4 | 12.9 | 31.0 | 23.0 | 15.9 | 13.5 | 9.2 | 10.4 | 9.8 | 1.8 |
| barrel temp., °C., zone A | 180 | 170 | 175 | 175 | 170 | 180 | 175 | 185 | 185 | 185 |
| barrel temp., °C., zone B | 190 | 170 | 185 | 185 | 180 | 200 | 195 | 200 | 200 | 200 |
| barrel temp., °C., zone C | 190 | 190 | 185 | 185 | 180 | 200 | 195 | 200 | 200 | 200 |
| barrel melt temp., °C. | 200 | 200 | 190 | 190 | 190 | 210 | 200 | 208 | 209 | 205 |
| pump size, cc per revolution | 1.17 | .584 | 1.17 | 1.17 | 1.17 | .297 | .297 | .297 | .297 | .16 |
| pump rpm | 8.1 | 11.8 | 16.7 | 12.2 | 7.6 | 18.7 | 16.1 | 6.1 | 4.8 | 3.8 |
| pump temp., °C. | 175 | 180 | 175 | 175 | 175 | 175 | 175 | 190 | 190 | 190 |
| pump melt temp., °C. | 185 | 187 | 180 | 180 | 180 | 186 | 183 | 197 | 198 | 195 |
| block temp., °C. | 180 | 180 | 175 | 175 | 175 | 180 | 180 | 190 | 190 | 190 |
| clamp temp., °C. | 185 | 180 | 180 | 175 | 175 | 185 | 180 | 200 | 200 | 200 |
| adapter temp., °C. | 185 | 180 | 180 | 175 | 175 | 185 | 180 | 200 | 200 | 200 |
| filter type | flat | flat | flat | flat | flat | flat | flat | CDL | CDL | CDL |
| filter screen, microns | 20 | 20 | 20 | 20 | 10 | 5 | 5 | 5 | 5 | 1 |
| diameter of spinneret orifices | 2.3 | 2.3 | 1.25 | 1.25 | .75 | .75 | .75 | .50 | .304 | .304 |
| no. of spinneret orifices | 1 | 1 | 4 | 4 | 4 | 4 | 4 | 4 | 4 | 4 |
| spinneret temp, °C. | 170 | 170 | 165 | 165 | 175 | 175 | 170 | 190 | 190 | 190 |
| spinneret melt temp., °C. | 177 | 173 | 170 | 179 | 168 | 179 | 165 | 181 | 180 | 180 |
| lb/hr output, per orifice | .92 | .66 | .47 | .34 | .21 | .13 | .11 | .04 | .034 | .014 |
| chimney length, cm | 68 | 68 | 23 | 23 | 8 | — | — | — | — | — |
| air gap, cm | 2 | 2 | 12 | 8 | 5 | 1 | 1 | 1 | 1 | 1 |
| quench bath temp., °C. | 80 | 75 | 75 | 75 | 65 | 50 | 40 | 30 | 30 | 30 |
| driven roller, rpm | 3 | 3 | 4 | 4 | 5 | 4.5 | 7 | 7 | 7 | 7 |
| draw bath temp, °C. | 98 | 98 | 97 | 97 | 86 | — | — | — | — | — |
| first heating chamber temp, °C. | — | — | — | — | — | 100 | 100 | 110 | 110 | 110 |
| first godet, mpm | 5.5 | 5.5 | 6.3 | 6.3 | 7.3 | 7.3 | 10.3 | 9.9 | 10.0 | 10.0 |
| second godet, mpm | 36.2 | 37.5 | 42.0 | 42.0 | 48.7 | 47.4 | 67.3 | 60.3 | 60.0 | 60.0 |
| draw ratio | 6.6 | 6.8 | 6.6 | 6.6 | 6.7 | 6.5 | 6.5 | 6.1 | 6 | 6 |
| Stretching Orienting) Operation | | | | | | | | | | |

TABLE I-continued

CONDITIONS OF MANUFACTURING VARIOUS SIZES OF POLYPROPYLENE MONOFILAMENT SUTURE

| Process Conditions | Example | | | | | | | | | |
|---|---|---|---|---|---|---|---|---|---|---|
| | 1 | 2 | 3 | 4 | 5 | 6 | 7 | 8 | 9 | 10 |
| | Suture Size | | | | | | | | | |
| | 2 | 1 | 0 | 2/0 | 3/0 | 4/0 | 5/0 | 6/0 | 7/0 | 8/0 |
| Second (Optional) Heat Treating Operation | | | | | | | | | | |
| second heating chamber temp, °C. | — | — | — | — | — | — | — | 70 | 70 | 70 |
| third godet | — | — | — | — | — | — | — | 63.5 | 63.4 | 63.4 |
| shrinkage as % recovery of stretched length | — | — | — | — | — | — | — | 95 | 95 | 95 |
| Equilibration Operation | | | | | | | | | | |
| holding period for equilibration, days | 4 | 4 | 4 | 4 | 4 | 4 | 4 | 4 | 4 | 4 |
| Annealing Operation | | | | | | | | | | |
| annealing temp., °C. | 110 | 110 | 110 | 110 | 110 | 110 | 110 | 110 | 110 | 110 |
| duration of annealing, min. | 10 | 10 | 10 | 10 | 10 | 10 | 10 | 10 | 10 | 10 |
| shrinkage as % recovery of stretched length | 85 | 85 | 85 | 90 | 90 | 90 | 90 | — | — | — |

What is claimed is:

1. A medical device comprising a suture-needle combination comprising a filament spun from a composition containing a syndiotactic polypropylene.

2. The medical device of claim 1 wherein the syndiotactic polypropylene possesses a weight average molecular weight of from about 15,000 to about 400,000 and a number average molecular weight of from about 4,000 to about 200,000.

3. The medical device of claim 1 wherein the syndiotactic polypropylene possesses a weight average molecular weight of from about 20,000 to about 300,000 and a number average molecular weight of from about 5,000 to about 150,000.

4. The medical device of claim 1 wherein the syndiotactic polypropylene possesses a melt flow index in g/10 min of from about 2 to about 20.

5. The medical device of claim 1 wherein the syndiotactic polypropylene possesses a melt flow index in g/10 min of from about 3 to about 5.

6. The medical device of claim 1 wherein the syndiotactic polypropylene is present in a blend with at least one other thermoplastic polymer.

7. The medical device of claim 6 wherein the blend contains from about 5 to about 95 weight percent syndiotactic polypropylene, the balance of the blend containing the other thermoplastic polymer or polymers.

8. The medical device of claim 6 wherein the blend contains from about 20 to 80 weight percent syndiotactic polypropylene, the balance of the blend containing the other thermoplastic polymer or polymers.

9. The medical device of claim 1 wherein the syndiotactic polypropylene is present in a blend with isotactic polypropylene, stactic polypropylene or both.

10. The medical device of claim 9 wherein the blend contains from about 5 to about 95 weight percent syndiotactic polypropylene, the balance of the blend containing isotactic polypropylene, atactic polypropylene or both.

11. The medical device of claim 9 wherein the blend contains from about 20 to about 80 weight percent syndiotactic polypropylene, the balance of the blend containing isotactic polypropylene, atactic polypropylene or both.

12. A method of suturing tissue comprising:
providing a suture-needle combination wherein said suture comprises a filament spun from a composition containing a syndiotactic polypropylene;
piercing tissue with said needle of said suture-needle combination; and
drawing said suture at least partially through the tissue.

* * * * *